United States Patent
Edelmann et al.

(10) Patent No.: US 9,268,126 B2
(45) Date of Patent: Feb. 23, 2016

(54) OBSERVATION AND ANALYSIS UNIT (75) Inventors: Martin Edelmann, Aalen (DE);
Christian Thomas, Ellwangen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 135 days.

(21) Appl. No.: 13/395,636

(22) PCT Filed: Aug. 20, 2010

(86) PCT No.: PCT/EP2010/062169
§ 371 (c)(1),
(2), (4) Date: Mar. 12, 2012

(87) PCT Pub. No.: WO2011/032802
PCT Pub. Date: Mar. 24, 2011

(65) Prior Publication Data
US 2012/0168623 A1 Jul. 5, 2012

(30) Foreign Application Priority Data
Sep. 18, 2009 (DE) .......................... 10 2009 041 993

(51) Int. Cl.
*G02B 21/36* (2006.01)
*H01J 37/22* (2006.01)
(Continued)

(52) U.S. Cl.
CPC .......... *G02B 21/367* (2013.01); *G01N 23/2252* (2013.01); *H01J 37/228* (2013.01); *H01J 37/165* (2013.01)

(58) Field of Classification Search
CPC .......... G01N 23/2252; G01N 23/2251; G01N 23/225; H01J 37/28; H01J 37/165; H01J 37/256; H01J 37/3005; H01J 37/252; H01J 37/228; G02B 21/367
USPC ......... 250/306, 305, 281, 288, 310, 282, 307, 250/492.3
See application file for complete search history.

(56) References Cited

U.S. PATENT DOCUMENTS 2,944,172 A  7/1960 Opitz et al.
2,991,362 A * 7/1961 Schumacher ................. 250/310
(Continued)

FOREIGN PATENT DOCUMENTS

DE    1119428    12/1961
DE    19845329 A1    9/1999
EP    0849765 A2    6/1998

OTHER PUBLICATIONS http://physics.nist.gov/PhysRefData/XrayMassCoef/ElemTab/z82.html, downloaded Mar. 31, 2015.*
(Continued)

*Primary Examiner* — Wyatt Stoffa
(74) *Attorney, Agent, or Firm* — Patterson Thuente Pedersen, P.A.

(57) ABSTRACT

An observation and analysis unit that magnifies an image of a sample and further accomplishes the evaluation and analysis thereof. The observation and analysis unit includes a light-microscopic device designed for the magnified imaging and optical evaluation of the sample and a sample analyzer that analyzes selected regions of the sample. The sample analyzer includes an electron source from which an electron beam can be directed to a region of the sample selected by use of the light-microscopic device. The sample analyzer further includes an X-ray detector designed to detect X-ray radiation generated by the interaction of the electron beam with the sample material. The unit further includes an actuation and evaluation unit that generates control commands for the light-microscopic device and the electron source and spectrally analyzes the X-ray radiation.

17 Claims, 6 Drawing Sheets

(51) Int. Cl.
*G01N 23/225* (2006.01)
*H01J 37/16* (2006.01)

(56) References Cited

U.S. PATENT DOCUMENTS

| | | | |
|---|---|---|---|
| 3,005,098 A * | 10/1961 | Buschmann et al. | 250/310 |
| 3,813,544 A * | 5/1974 | Franzen et al. | 250/281 |
| 3,919,548 A * | 11/1975 | Porter | 378/45 |
| 4,537,477 A * | 8/1985 | Takagi et al. | 250/311 |
| 4,663,511 A * | 5/1987 | Tallman | 219/121.13 |
| 5,192,866 A * | 3/1993 | Komi | 850/7 |
| 5,483,065 A * | 1/1996 | Sato et al. | 250/310 |
| 5,740,223 A * | 4/1998 | Ozawa et al. | 378/161 |
| 5,877,498 A * | 3/1999 | Sugimoto et al. | 250/310 |
| 5,905,266 A | 5/1999 | Larduinat et al. | |
| 5,990,480 A | 11/1999 | Yamada et al. | |
| 6,118,123 A * | 9/2000 | Notoya | 850/9 |
| 6,452,177 B1 * | 9/2002 | Feldman et al. | 850/9 |
| 6,590,210 B1 | 7/2003 | Essers | |
| 6,765,202 B1 * | 7/2004 | Hohn | 250/310 |
| 6,953,939 B2 * | 10/2005 | Abe et al. | 250/441.11 |
| 7,720,192 B2 * | 5/2010 | Hegeman et al. | 378/44 |
| 7,868,290 B2 * | 1/2011 | Koops et al. | 250/311 |
| 8,115,180 B2 * | 2/2012 | Doemer et al. | 250/442.11 |
| 8,178,849 B2 * | 5/2012 | Drexel | 250/396 ML |
| 8,283,641 B2 * | 10/2012 | Donitz et al. | 250/492.1 |
| 8,350,227 B2 * | 1/2013 | Doemer et al. | 250/442.11 |
| 8,362,443 B2 * | 1/2013 | Drexel | 250/396 ML |
| RE44,035 E * | 3/2013 | Schamber et al. | 250/492.1 |
| 2001/0022830 A1 * | 9/2001 | Sommer et al. | 378/45 |
| 2003/0025087 A1 * | 2/2003 | Schamber et al. | 250/491.1 |
| 2003/0053048 A1 * | 3/2003 | Bennett et al. | 356/301 |
| 2004/0144928 A1 * | 7/2004 | Abe et al. | 250/441.11 |
| 2005/0134841 A1 * | 6/2005 | Vacz-Iravani et al. | 356/237.4 |
| 2006/0118733 A1 * | 6/2006 | Kiyohara et al. | 250/491.1 |
| 2009/0002695 A1 * | 1/2009 | Saito et al. | 356/237.4 |
| 2011/0115129 A1 * | 5/2011 | Straw et al. | 264/400 |
| 2012/0103945 A1 * | 5/2012 | Straw et al. | 219/121.35 |
| 2014/0158883 A1 * | 6/2014 | Zewail | 250/305 |

OTHER PUBLICATIONS

Company publication of Carl Zeiss: "Shuttle & Find for Life Sciences. Enabling Productivity in Correlative Microscopy", as of Jan. 1, 2010 (in English); 8 pages.
Pfeifer, Dr. Andreas; Carl Zeiss SMT—NTS Division; "Vom Photon zum Ion—Einsatz höchstauflösender Analyseverfahren in der Mikroeektronik"; date Oct. 15, 2009, 20 pages.
International Search Report for PCT/EP2010/062169; international filing date Aug. 20, 2012; mailed Dec. 2, 2010; 4 pages.
First Examination Report for Priority Application DE102009041993.4 of Jul. 29, 2010, 2 pages.

* cited by examiner

OBSERVATION AND ANALYSIS UNIT

PRIORITY CLAIM

The present application is a National Phase entry of PCT Application No. PCT/EP2010/062169, filed Aug. 20, 2010, which claims priority from German Application Number 102009041993.4, filed Sep. 18, 2009, the disclosures of which are hereby incorporated by reference herein in their entirety.

FIELD OF THE INVENTION

The invention relates to an observation and analysis unit provided with means for the magnified imaging of a sample and with means for the evaluation and analysis thereof.

BACKGROUND

Observation devices suitable for the magnified imaging and optical evaluation of samples are actually known in the form of light microscopes. With light microscopes, a resolving power is achieved that is about 1000 times that of the human eye. In addition to this relatively high resolution, it is necessary in many light-microscopical examinations to carry out a detailed analysis of the chemical element composition of particular regions of the sample, identified by means of the light microscope, e.g., in order to characterize undesirable inclusions in metallurgical samples.

In the prior art, such detailed analyses are, as a rule, carried out with a scanning electron microscope, which, in imaging the sample surface by means of secondary electrons, yields an even substantially higher resolution of better than 1 nanometer (nm). In chemical analyses by X-ray spectroscopy with the scanning electron microscope, however, the best possible resolution is within a range of 0.5 to 2 micrometers ($\mu$m) and is determined by the volume of interaction of the electron beam with the sample.

For examining one and the same sample, thus, it is necessary to change from one instrument to another, which involves a considerable interruption of the work flow, as the examination of the sample in the scanning electron microscope takes place in a vacuum, for which reason the sample taken from the light microscope first has to be brought into a vacuum through a lock, after which the sample region of interest has be found again in the scanning electron microscope and positioned.

Added to this may be waiting time for the availability of a scanning electron microscope, and furthermore there is the risk of the sample getting damaged during transfer between the instruments. Moreover, a scanning electron microscope is a relatively expensive investment, the technical capabilities of which are required to a limited extent only, if at all, for solving the problem mentioned above, i.e. the analysis of a chemical element composition after light-microscopical examination.

U.S. Pat. No. 6,452,177, for example, describes an electron-beam-based material analysis system which is suitable especially for examinations under atmospheric pressure. This system has the drawback that it is unfit for microscopical observation of the sample. Moreover, the sample region in which the material is to characterized is dot-shaped and relatively large, i.e. >100 $\mu$m; there is no shielding against the X-ray radiation, and the time required for a measurement is relatively long. Another drawback is that the electrons escape from the vacuum of the electron source to the surrounding atmosphere through an electron-transparent membrane. This leads to increased scattering, which is a disadvantage especially for examinations at high resolution. Furthermore, the electron scattering produces X-ray radiation, which is superimposed on the signal measured of the sample, thus degrading the quality of the measurement signal.

SUMMARY OF THE INVENTION

Departing from this, the invention addresses the problem of creating an observation and analysis unit with which an analysis of a sample by electron-beam excitation can be accomplished immediately after or during its light-microscopically magnified imaging.

According to the invention, such an observation and analysis unit comprises
  a light-microscopical device designed for the magnified imaging and optical evaluation of a sample,
  means for the analysis of selected regions of the sample, provided with an electron source from which an electron beam can be directed to a region of the sample selected by means of the light-microscopic device, and with an X-ray detector designed to detect the X-ray radiation generated by the interaction of the electron beam with the sample material, and
  an actuation and evaluation unit which generates control commands for the light-microscopic device, the electron source and/or sample positioning, and spectrally analyzes the X-ray radiation.

In contrast to prior art, the unit according to the invention permits both the light-microscopical and the electron-beam-excited examination to be carried out without requiring an interruption of the work flow because of any changing between two physically separated instruments. As an added advantage, X-ray analysis with the invented unit, unlike analysis with a scanning electron microscope, does not need a vacuum environment, because the sample is examined in air or in the presence of some other gas. Moreover, higher throughput rates are possible when a series of samples are to be analyzed. During analysis by application of electron beam source and X-ray detector, the sample is surrounded by some gas below or near atmospheric pressure.

In an example embodiment, the invented observation and analysis unit is provided with control means for moving the sample relatively to the observation ray path of the light-microscopical unit, the electron beam and/or the X-ray detector. The control means are connected to the actuation and evaluation unit, so that control commands for position changes can be generated and issued either on the basis of arbitrary specifications or as a function of the result of observation and/or analysis.

To prevent any hazard due to unwanted propagation of the X-rays, a shielding means that is opaque to X-rays can be provided. Furthermore, a shutter or filter may be provided which blocks the ray path of the light-microscopical unit to the X-rays at least when the electron source is in switched-on state.

It is also feasible and within the scope of the invention that the shielding means is gas-tight and that an arrangement for feeding some gas, preferably helium, into the space between sample and electron source is provided.

Feeding gas into the space between sample and electron source is feasible and advantageous also independent of the design of a shielding means.

Furthermore, the observation and analysis unit should be provided with means for focusing the electron beam on the selected region of the sample. In that respect, a tubule may be provided between the electron source and the sample, through which the electron beam is guided to the sample. Preferably, a device for varying the distance between the sample surface and the electron beam outlet port of the tubule is provided.

To enable the electron beam to be targeted at the sample in a straightforward way, a light beam, preferably a laser beam, run parallel to the direction of the electron beam and is visible to the operator of the observation and analysis unit. With such a—preferably laser-optical—targeting beam in the visible wavelength range, the spot of impact of the electrons on the sample can easily be marked or calibrated. Alternatively, for the same purpose, a phosphorescent element can be provided for marking or calibrating the spot of electron impact.

It is of particular advantage if one or several objectives allocated to the light-microscopical unit are arranged, together with the electron source and/or the X-ray detector, on a change-over device by means of which they can be interchanged and selected for active use. In another favorable embodiment of the invention, the area for visual observation of the sample by means of the light-microscopical unit on the one hand, and the area for analysis of the sample by means of the electron beam and the X-ray detector on the other hand, may be arranged within the observation and analysis unit, but physically separated from one another.

In a special embodiment of the invention, a light microscope is provided with
  an electron source, from which an electron beam is directed at the sample in addition to, or as an alternative to, the illumination ray path coming from the objective of the light microscope,
  an X-ray detector, which detects the X-ray radiation generated on account of the interaction of the electron beam with the sample, and,
  arranged downstream of the X-ray detector, an evaluation device which spectrally analyzes the X-ray radiation.

Here again, during analysis by means of the electron beam source and the X-ray detector, the sample is surrounded by some gas below or near atmospheric pressure.

It is to be understood that the subject matter of the invention includes all technically equivalent means and their operating relationships. This includes, for example, means for the analysis of selected regions of the sample by means of ions that, emitted by an ion source, are used to excite the sample substance instead of excitation by electrons.

Another example is examination of the luminescence generated in the sample by the electron beam, using a luminescence detector operating via the light microscope, or a separate detector.

With the invented observation and analysis unit, a microscopically small, spatially resolved sample region can be analyzed, with a spot analysis being possible within a few seconds thanks to the radiant intensities provided.

Further advantages of the invented arrangement, in addition to the capability of direct sample analysis at the light microscope ray path, are given by the fact that selection of the desired sample region is possible directly in the light microscope image. By means of the optional shifting of the sample relative to the electron source, the sample region selected can be centered under the electron source, and the X-ray spectrum can be recorded and evaluated automatically.

It is possible advantageously to achieve a compact design of the electron source and the X-ray detector and to implement scanning of the sample and/or the electron beam, whether for mapping or for increasing the spatial resolution by means of deconvolution.

BRIEF DESCRIPTION OF THE DRAWINGS

Below, the invention will be explained in greater detail with reference to exemplary embodiments. In the accompanying drawings.

DETAILED DESCRIPTION

Figure 1:
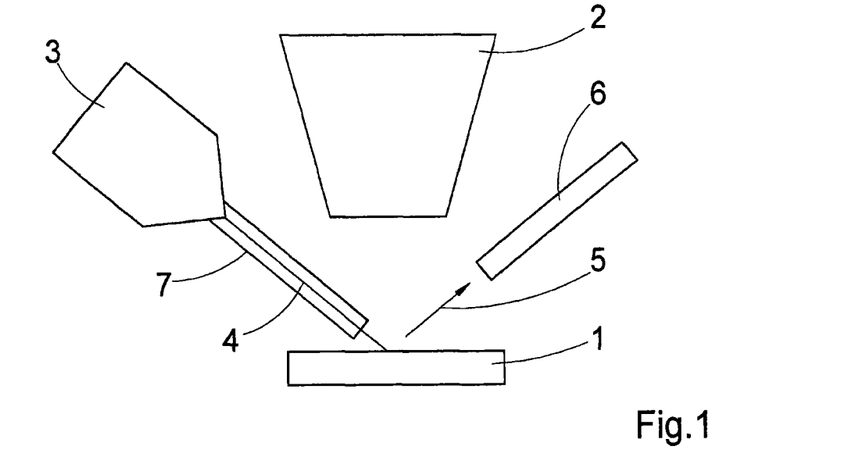
FIG. 1 depicts the design principle of the invented observation and analysis unit.

FIG. 1 shows the design principle of the invented observation and analysis unit with a facility for light-microscopical observation, and subsequent direct sample analysis. For the sake of clarity, only one microscope objective 2 of the light-microscopical unit provided for the magnified imaging and optical evaluation of a sample 1 is shown. As mentioned in the beginning, light microscopes and their ray paths are known and need no further explanation here.

In FIG. 1 one can see an electron source 3, which generates an electron beam 4 that can be directed at the sample 1 below the microscope objective 2. On account of the interactions of the electron beam 4 with the sample 1, X-ray radiation 5 is generated that is characteristic of the chemical composition of the sample 1 within the interaction volume.

The X-ray radiation emitted by the sample 1 under electron irradiation is spectrally characterized by an X-ray detector 6. The X-ray detector 6 employed may be a cooled Si(Li) detector or a silicon drift detector as commonly used in electron microscopes.

The detecting direction of the X-ray detector 6 preferably forms the smallest possible angle with the line normal to the surface of the sample 1 in order to maximize the detection efficiency especially as far as light elements contained in the sample are concerned. For this purpose, it is advantageous to arrange either the electron source 3 or the X-ray detector 6 in or near the ray path of the microscope objective 2 of the light-microscopical unit. The X-ray detector 6 is preferably arranged in such a way that it captures as many X-ray quanta as possible. For this purpose, it is placed as close as possible to the electron impact site, so that a large solid angle is captured.

In connection with the problem to be solved, a compact electron source 3 is suited, which consists of an electron emitter and an electrode arrangement for acceleration and focusing (not shown in the drawing). The electron energy is, e.g., >15 keV.

The requirements the electron beam 4 must satisfy are less exacting than those to be met by a scanning electron microscope. For example, a beam width of a few micrometers (μm)

is absolutely sufficient, because, due to the energy used for analysis, the spatial resolution, which is determined by the interaction volume, is not any better as a rule. Moreover, a relatively small beam diameter gets immediately enlarged as the electrons are scattered in air. Furthermore, the electron beam 4 may remain permanently aligned and need not be moved across the sample 1 in a scanning mode.

Within the electron source 3 there is a vacuum, so that free electrons can be generated and focused with the fewest possible scatter processes. The vacuum is generated by a multi-stage, e.g., two-stage pump system, which forms a unit with the electron source 3 and consists of a backing vacuum pump and a high-vacuum pump (not shown on the drawing). The backing vacuum pump is connected to the lower end of the electron source 3, which faces the sample 1, and there is connection to the high-vacuum pump, which is connected to the upper end of the electron source 3, which faces away from the sample 1. In this way, a pressure gradient is produced within the electron source unit, with the pressure decreasing from the lower to the upper end.

Placement of pressure-limiting apertures within the pump system, the pressure gradient can be precisely adapted. As a consequence, the electron source is configured in such a way that the free electrons are generated in the upper area and then focused by means of an electron lens system (not shown) towards the lower end, where they leave the electron source 3 through a suitable device, e.g., through a tubule 7.

At the outlet port of the tubule 7, a pressure-limiting aperture is provided, so that the sample 1 can be analyzed under ambient pressure. The pressure-limiting aperture may consist of several stages. To improve the efficiency of the pump system, the tubule 7 may be of a tapered design.

The distance between the sample 1 and the electron outlet port at the tubule 7 may be, e.g., <0.5 mm. To minimize this distance, the tubule 7 itself or the entire electron beam unit may be arranged so as to be movable towards the sample 1. Optionally, controlling this distance may be provided by mechanical contact between sample 1 and tubule 7. In case of conductive samples 1, this distance can be determined and controlled on the basis of an electric resistance or impedance measurement.

The electron beam 4 is directed at a selected region within the field of view of the microscope objective 2, so that the electrons hit the sample in this region. On collision of the electrons with the atoms of the sample material, electrons are knocked out of the inner shells of the atoms. Such a state is unstable, which is why the missing electrons are immediately replaced by electrons richer in energy from higher orbitals. The energy difference is liberated in the form of X-ray quanta. The X-ray radiation 5 generated thereby is characteristic of the transitions and the respective atoms, and thus, for the elements existing in the sample region.

Figure 2:
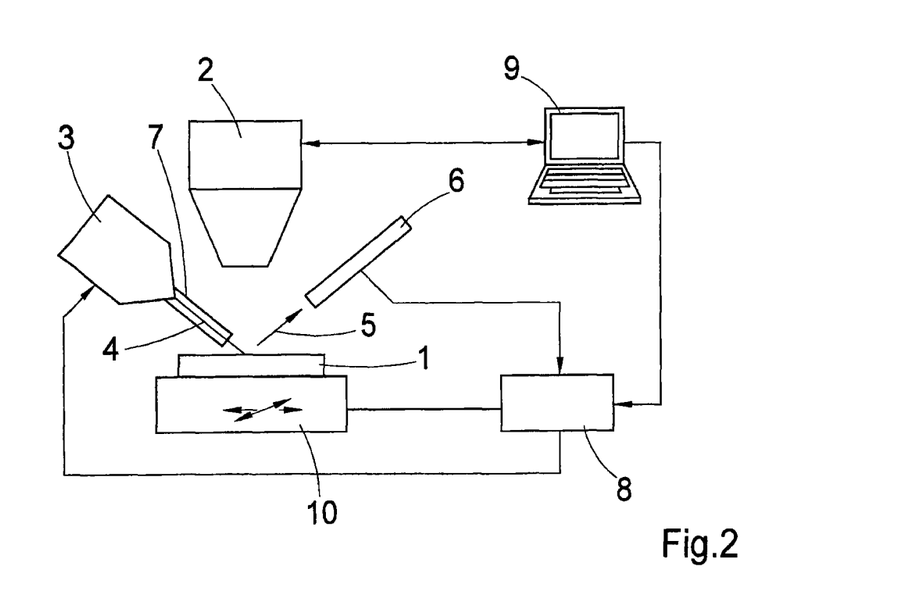
FIG. 2 is an extended view of the design principle of the invented observation and analysis unit following FIG. 1.

This X-ray radiation 5 is detected by the X-ray detector 6. As shown in FIG. 2, the signal of the X-ray detector 6 is applied to an actuation and evaluation unit 8, where it is evaluated and can be analyzed, e.g., by use of suitable software, whereupon the element distribution in the sample region irradiated is visually displayed on a monitor or printed out.

The entire system is supervised by a central computing unit 9, which can control the light-microscopical unit and receive and process its data, and which is, via the actuation and evaluation unit 8, is connected with the electron source 3, the X-ray detector 6 and the drives of a movable sample stage 10, which carries the sample 1. It is thus possible to operate the observation and analysis unit by use of a single software program.

Figure 3:
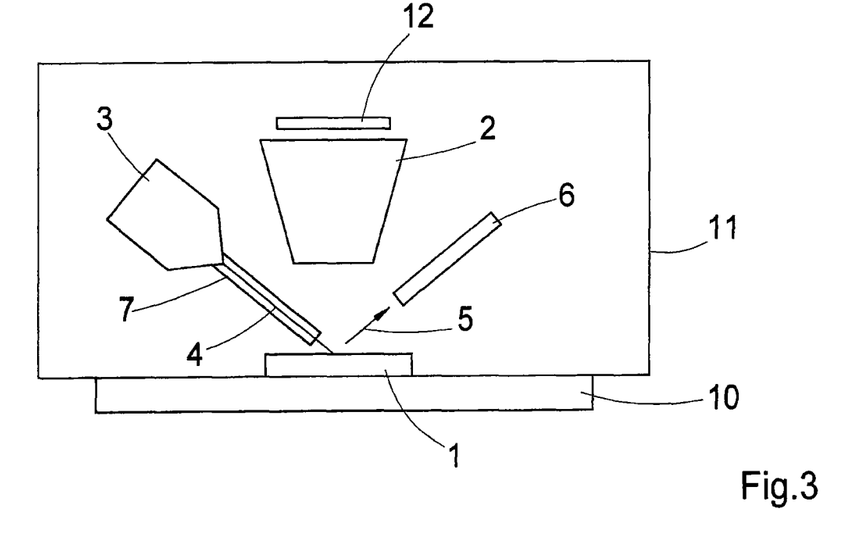
FIG. 3 depicts an example embodiment based on the design principle according to FIG. 1.

Furthermore, as shown symbolically in FIG. 3, the unit consisting of the microscope objective 2, the electron source 3 and the X-ray detector 6 may be enclosed by a shielding 11, which shields the X-ray radiation 5 off from the outside.

The shielding 11 may, for example, be permanently installed, in which case it prevents X-ray radiation 5 from leaking out at any time without being actuated, so that the electron source 3 can be actuated at any time without danger. Alternatively, the shielding 11 may be designed in such a way that it has to be manually closed every time before a sample analysis. In this case, the status of the shielding 11 is detected by the actuation and evaluation unit 8, and the electron source 3 is actuated only if manual closure has been carried out correctly. As an alternative, it is also feasible that the shielding 11 be controlled by actuation and evaluation unit 8, so that closure is effected automatically before the electron source 3 is switched on. In this version, the atmospheric pressure within the shielding 11 is maintained.

In this connection, the observation and analysis unit can be provided with a gas feeding means in addition, which makes it possible to flood the area between sample 1 and electron source 3 with a gas, which causes a decrease in the scattering of the electrons while retaining the atmospheric pressure. Gases having atomic numbers lower than nitrogen and oxygen, the main constituent elements of air, are especially suitable for that purpose. Helium, for example, is a particularly preferable gas; being a noble gas, it is harmless and chemically low-reactive. To minimize gas consumption, the outer confinement by the shielding 11, which should be dimensioned as small as possible, can be sealed so that only the least possible amount of gas can leak out.

In this embodiment, the possibility of visual light-microscopical observation exists until immediately before the electron source 3 is switched on. As soon as the electron source 3 is switched on, a shutter 12, controlled by the actuation and evaluation unit 8, occludes the optical ray path to protect the user against the X-ray radiation 5. Alternatively, the shutter 12 can be replaced with a permanently installed X-ray protective glass, so that light-microscopical observation need not be interrupted at any time.

Figure 4:
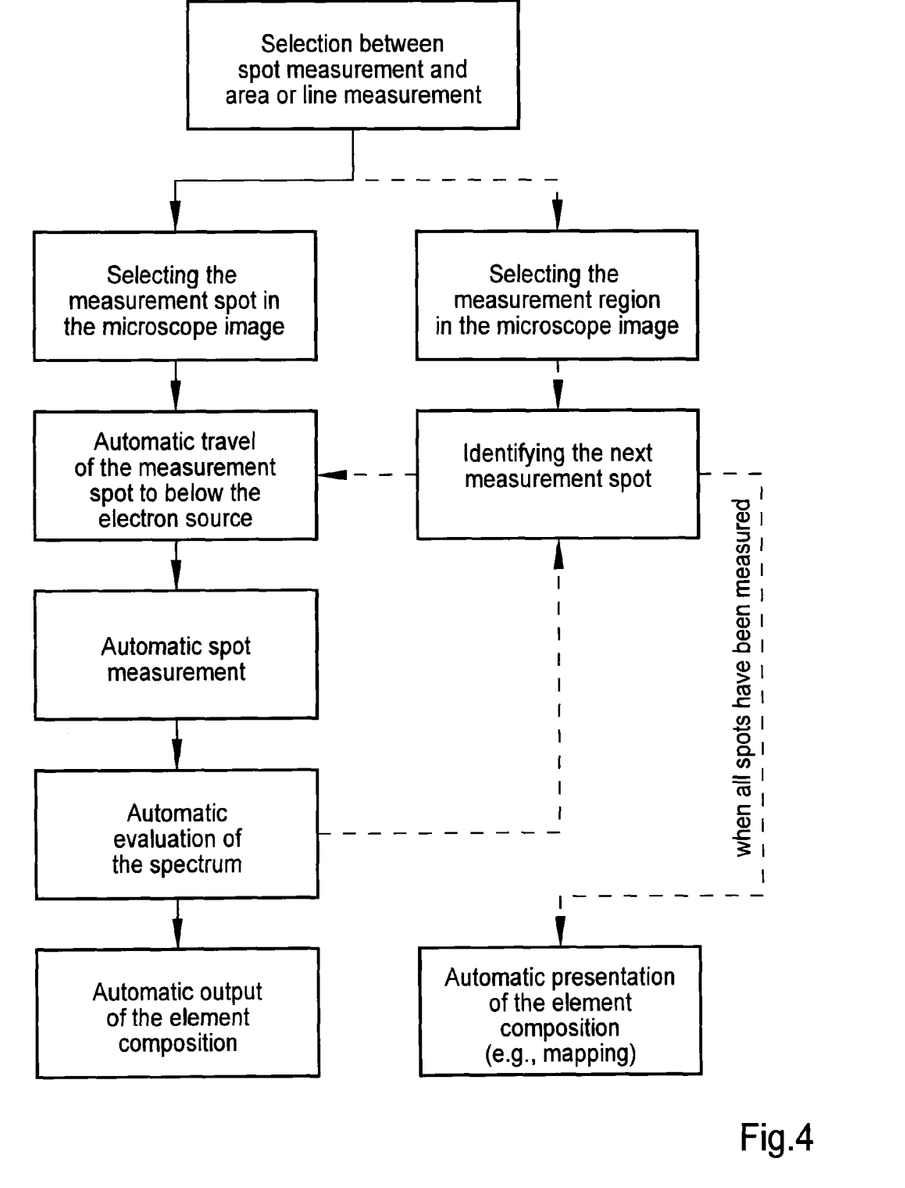
FIG. 4 is a flow chart depicting the example of process sequence in the observation and analysis of a sample with the invented unit.

FIG. 4 shows the sequence of processes in direct sample observation by use of the light-microscopical unit. The flow chart makes a difference between measurement in a single spot (solid-line connections) and measurement within a certain region (broken-line connections), for example, along a line or within an area. Therefore, the sequence of processes starts with selecting between the two ways. Measurement in a region consists of measurements of several individual spots. Because of the finite resolution, a spot measurement actually means a measurement in a region of several micrometers (μm), resulting from the dissipation volume of the electron beam 4. Nevertheless, this is regarded as a spot measurement here. A measurement across a region of several spots is given if the electron beam 3 has to be positioned from one spot on the sample to another, necessitating a relative movement between the two spots.

For measurement in a spot, the spot in which the element analysis is to be carried out, is selected in the light-microscopical image after or during its being recorded. This may be done, e.g., by clicking on the spot in the image with a mouse pointer displayed by the software. Once the measurement spot has been identified, the sample 1 is automatically positioned by movement of the sample stage 10 so that the spot to be measured on the sample 1 is at the focus of the electron beam 4. With positioning accomplished, the electron source 3 is automatically activated by the actuation and evaluation unit 8, and the electron beam 4 is directed at the selected sample detail.

The characteristic X-ray radiation 5 produced in this place is detected by the X-ray detector 6 and read out via the actuation and evaluation unit 8. By means of the software, the spectrum measured is automatically analyzed, and the exact element composition in the measurement spot selected is output as a result. The time from selecting up to the output of the result essentially depends on the beam current and the sensitivity of the X-ray detector 6; at maximum, it amounts to several seconds.

In a measurement in a larger region consisting of several measuring spots, at first individual measuring spots in this region are identified that are to be moved to in succession. A list of these spots is created in the computing unit 9. Thereupon, the electron beam 4 is automatically positioned to the first spot of the list, and the measurement is carried out as described above, so as to obtain the element composition in this spot. The procedure is then repeated for all spots that make up the measuring region. When all measuring spots have thus been processed, the spatial distribution of elements is displayed as a result. This can be accomplished, e.g., by a colored or other graphic overlay on the light-microscopical image.

Figure 5:
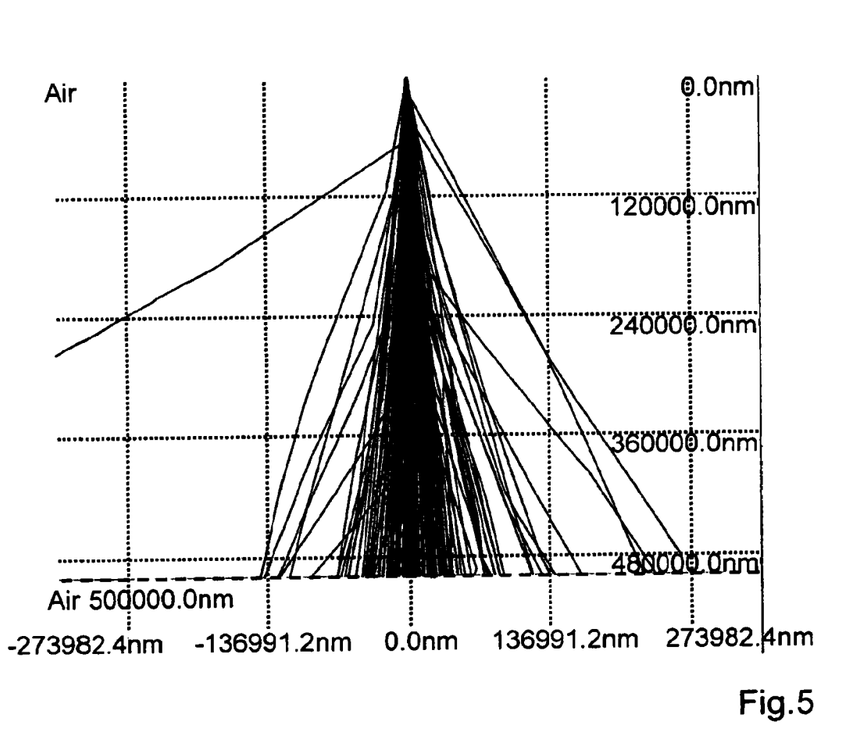
FIG. 5 is a Monte Carlo simulation of the interactions of an electron beam with a sample.

FIG. 5 shows a Monte Carlo simulation of the interactions of an electron beam 4 of 30 keV energy and 1 μm beam diameter in air at an atmospheric pressure of 1 bar and a density of 1.293 kg/m$^3$ with the sample 1. After a path length of 500 μm, 97% of the electrons have lost less than 1 keV of energy, thus still having sufficient energy left to excite X-ray emission in a sample 1 placed below it. To be sure, the beam diameter increases due to scattering at the air molecules, but it still is less than 50 μm. By local feeding of helium instead of air into the space between the electron outlet port and the sample 1, scattering can be reduced and, thus, a smaller beam diameter be achieved.

Figure 6:
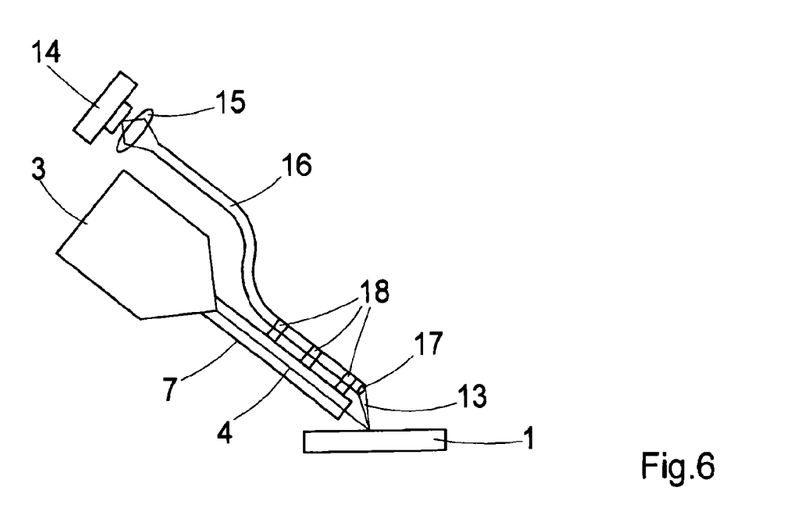
FIG. 6 depicts an embodiment with a device for the adjustment of the electron beam relative to the sample.

Supplementing FIG. 3, FIG. 6 shows an embodiment provided with a device for adjusting the electron beam 4 relative to the sample 1. For this purpose, a laser beam 13 is used, which marks the desired electron impact site on the sample 1. Generated by a laser diode 14, the laser beam 13 is coupled into an optical fiber 16 via an optical coupling system 15, the said optical fiber preferably being run above the tubule 7. At the end of the optical fiber 16 there is a microlens 17 for focusing the laser beam 13. The optical fiber 16 is connected with the tubule 7 by holders 18. This arrangement is adjusted in such a way that, with a minimum focal spot of the laser beam 13 on the sample 1, the electron impact site is visibly marked. A prior initial adjustment of the laser beam 13 relative to the electron source 3 can be done by means of a phosphorescent screen (not shown on the drawing), which also renders the electron impact site visible.

Figure 7:
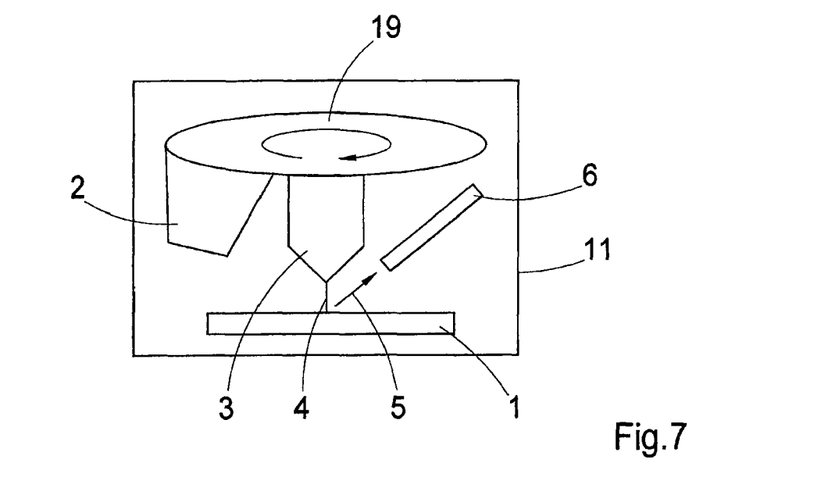
FIG. 7 depicts an example embodiment in which the electron source is of miniaturized design and can be integrated into a revolving objective nosepiece.

FIG. 7 shows another example embodiment, in which the electron source 3 is miniaturized to such an extent that it can be integrated into a revolving objective nosepiece 19 of the light-microscopical unit. In the revolving objective nosepiece 19, the electron source 3 is located in place of one of several microscope objectives 2.

In this case, X-ray analysis of the sample 1 simultaneously with light-microscopical observation is not possible, though, but the fast possible change-over between microscope objectives 2 and electron source 3 by the precise rotation of the revolving objective nosepiece 19 is not a disadvantage in that respect. An advantage is that the electron beam 4 hits the sample surface at a right angle, so that shading effects are avoided. Also, lateral positioning of the electron beam 4 does not depend on the distance between the electron source 3 and the sample 1 here, so that the electron source 3 needs to be adjusted only once, i.e. during installation.

The electron source 3 can be fixed to the revolving objective nosepiece 19 either directly or via a suitable adapter; for example, it may be provided with a matching thread so that it can be screwed right into the revolving objective nosepiece 19. The actuation and evaluation unit 8 and the vacuum pumps are located outside the revolving objective nosepiece 19 and are connected with the electron source 3 via supply lines for power supply, control signals and vacuum.

In the view presented by FIG. 7, the microscope objective 2 is inactive and laterally moved out of action, as are other microscope objectives 2 (not shown), whereas the electron source 3 is in working position. The X-ray detector 6 arranged on a side can be activated in this configuration. If, however, a microscope objective 2 instead of the electron source 3 is brought into the working position by a turn of the revolving objective nosepiece 19, both the electron source 3 and the X-ray detector 6 are switched to an inactive state.

Furthermore, during element analysis, the X-ray radiation 5 can optionally be screened towards the outside, as already explained in the context of FIG. 3.

Figure 8:
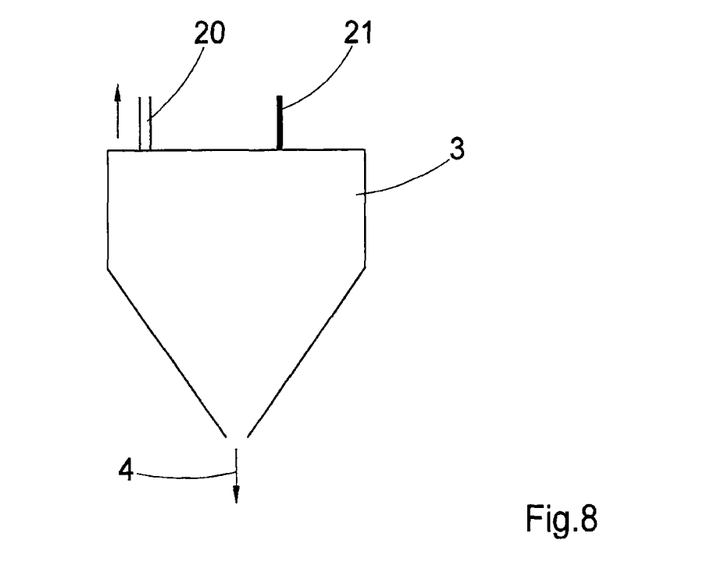
FIG. 8 depicts a miniaturized electron source to be installed into a revolving objective nosepiece, with its external interfaces.

The miniaturized electron source 3 to be integrated into a revolving objective nosepiece 19 is shown in FIG. 8. The external interfaces provided comprise a hose 20 for vacuum connection and electrical feed lines 21 for power supply and actuation of the electron source 3 and the electron lens system if provided. Individual components of the electron source 3 and of the electron lens system, which have to be very compact because of the limited space available, may be fabricated in a miniaturized manner in a microsystem technology known as MEMS (microelectromechanical system) technology.

To generate an electron beam having an energy of 30 keV, a simple electrode arrangement with an overall length of <3 mm is sufficient. For example, one uses an electron emitter to generate free electrons, which are then accelerated along the acceleration section and concentrated in a single lens before they exit through the aperture. In a highly simplified embodiment, one can do without the single lens and merely have the electron beam cut off by the aperture, although one has to put up with a lower current in this case.

The electron lens system may consist, e.g., of a system of conductive and insulating layers, with different potentials being applied to the conductive layers, so that the free electrons are concentrated, accelerated and focused by the fields generated. Further, the electron lens system is arranged towards the outlet port of the electrons, which constitutes a pressure-limiting aperture relative to the normal atmospheric pressure environment. The vacuum system within this electron source unit is not shown in detail here, but, as explained above, ideally it is a multi-stage vacuum system also provided with various pressure-limiting elements.

Optionally, also the X-ray detector 6 can be fitted in the revolving objective nosepiece 19 in place of a microscope objective 2 immediately next to the electron source unit. In this case, positioning the electron source automatically also positions the X-ray detector 6, and no extra means for lateral fixing of the X-ray detector 6 is required.

Figure 9:
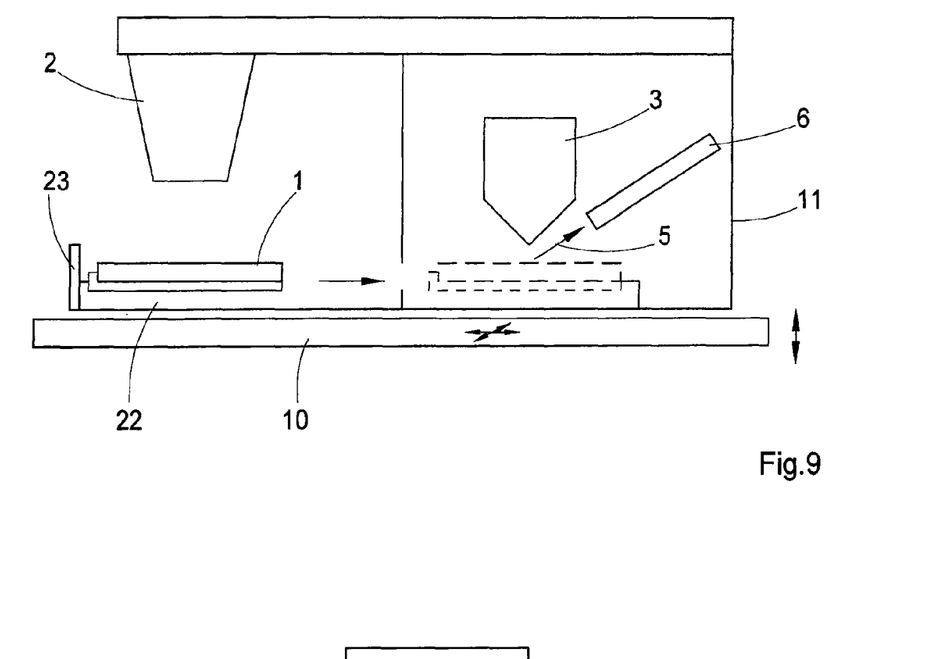
FIG. 9 depicts an embodiment in which the sample can, by means of a slide, be transferred from an area of the light-microscopical unit to a separate area for X-ray analysis.

FIG. 9 shows an embodiment in which the sample 1 can be moved out of the area of the microscope objective 2 by a slide 22 and transferred to a separate area for X-ray analysis. With this it is also possible to position the electron source 3 to a place vertically above the sample 1; in this case, the size and weight of the electron source 3 are less restricted than they are in the example according to FIG. 8.

Another advantage is that the light-microscopical unit, or at least the microscope objective 2, need not be integrated within the shielding 11. Nevertheless, the area for X-ray analysis is firmly joined directly to the light-microscopical unit. The slide 22 ensures fast transfer. Due to a fixed moving distance of the slide 22, which corresponds to the distance between microscope objective 2 and electron source 3, it is ensured that the detail of the sample 1 observed through the microscope objective 2 is identical to the detail analyzed in the area for X-ray analysis. Fast covering of the moving distance is made possible by suitable mechanical or electrically controlled stops. In addition to the one-dimensional movement of the slide, the arrangement can, as described above, comprise a sample stage 10, on which the slide moving device is permanently mounted, and which permits traveling to any position on the sample, whereas the slide device permits precise transfer of the sample positions traveled to.

The shielding 11 of the area for X-ray analysis is designed in such a way that, by means of a closing plate 23 fitted to the slide 22, it is closed automatically as soon as the sample 1 is in the measuring area.

Figure 10:
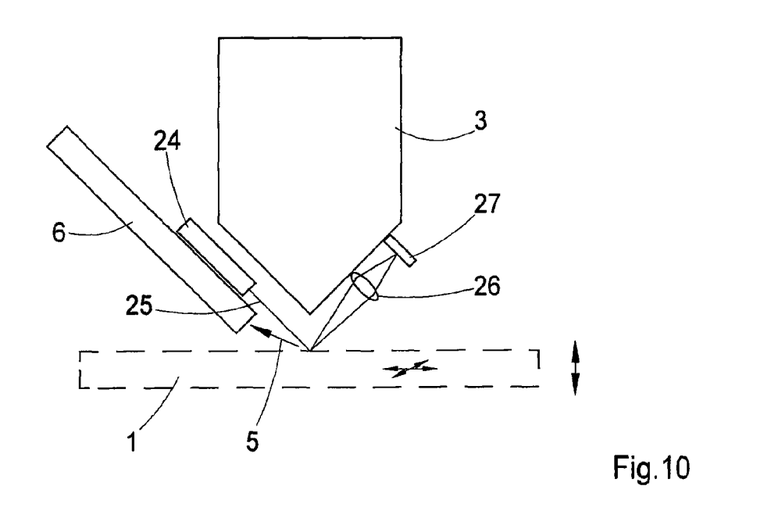
FIG. 10 depicts, supplementary to FIG. 9, the setting of the distance between the sample surface and the electron beam outlet port by means of laser triangulation.

Supplementing FIG. 9, FIG. 10 shows how the working distance between the sample 1 and the electron outlet port can be set by means of laser triangulation. For this purpose, a laser source 24 is arranged and adjusted in such a way that a laser beam 25 hits the electron impact site at the desired working distance. The laser spot is detected by a CCD sensor 27 via an optical imaging system 26. After sample transfer, a movement of the electron source 3 relative to the sample 1 is released by the signals of the CCD-Sensors 27, and the desired working distance is set.

FIG. 10 also shows a possible position of the X-ray detector 6. Preferably, however, the X-ray detector 6 occupies a position outside the drawing plane, e.g., normal to it, in order to leave sufficient space for providing the triangulation device.

LIST OF REFERENCE NUMBERS 1 sample
2 microscope objective
3 electron source
4 electron beam
5 X-ray radiation
6 X-ray detector
7 tubule
8 actuation and evaluation unit
9 computing unit
10 sample stage
11 shielding
12 shutter
13 laser beam
14 laser diode
15 optical coupling system
16 optical fiber
17 microlens
18 holders
19 revolving objective nosepiece
20 hose
21 supply lines
22 slide
23 closing plate
24 laser source
25 laser beam
26 optical imaging system
27 CCD sensor

What is claimed is:

1. An observation and analysis unit, comprising:
   a light-microscopical device, designed for magnified imaging and optical evaluation of a sample;
   an analyzer that analyzes selected regions of the sample including:
      an electron beam source that directs an electron beam to a region of the sample selected by application of the light-microscopical device;
      an X-ray detector, that detects X-ray radiation generated by interaction of the electron beam with material of the sample;
      an actuation and evaluation unit, that generates control commands for the light-microscopical device, the electron source and/or a sample positioning structure, and that spectrally analyzes the X-ray radiation;
      a shielding that prevents propagation of the X-ray radiation that is hazardous to persons, wherein the shielding encloses the electron beam source, the X-ray detector, and the sample;
      a structure for feeding a non-air gas to a space between the sample and the electron beam source within the shielding;
   wherein the sample is surrounded by a gas below or near atmospheric pressure, during analysis by application of the electron beam source and the X-ray detector; and
   the light-microscopical unit further comprising a revolving objective nosepiece, wherein the electron source is integrated into the revolving objective nosepiece.

2. The observation and analysis unit as claimed in claim 1, further comprising a control device that moves the sample relative to an observation ray path of the light-microscopical unit, the electron beam and/or the X-ray detector.

3. The observation and analysis unit as claimed in claim 2, in which the control device is operably connected with the actuation and evaluation unit.

4. The observation and analysis unit as claimed in claim 1, wherein the non-air gas comprises helium.

5. The observation and analysis unit as claimed in claim 1 wherein the shielding is gas-tight.

6. The observation and analysis unit as claimed in claim 5, wherein the non-air gas comprises helium.

7. The observation and analysis unit as claimed in claim 1, further comprising an electron beam focuser that focuses the electron beam on the selected region of the sample.

8. The observation and analysis unit as claimed in claim 1, further comprising a tubule between the electron beam source and the sample, through which tubule the electron beam is directed to the sample.

9. The observation and analysis unit as claimed in claim 8, further comprising structure that varies a distance between the sample and an electron beam outlet port at the tubule.

10. The observation and analysis unit as claimed in claim 1, further comprising a shutter or filter, which, at least when the electron beam source is switched on, blocks a ray path of the light-microscopical unit to X-ray radiation, so that danger from the X-ray radiation during visual observation of the sample is inhibited.

11. The observation and analysis unit as claimed in claim 1, further comprising an electron beam aligner that aligns the electron beam relative to the sample by directing a light beam in a visible wavelength range directed substantially parallel to a direction of the electron beam.

12. The observation and analysis unit as claimed in claim 11, wherein the light beam comprises a laser beam.

13. The observation and analysis unit as claimed in claim 1, further comprising an exchanger holding at least one microscope objective allocatable to the light-microscopical unit, the electron source, the X-ray detector or both the electron source and the X-ray detector.

14. The observation and analysis unit as claimed in claim 1, wherein an area for visual observation of the sample with the light-microscopical unit and an area for analysis of the sample with the electron beam and the X-ray detector are located separately from one another.

15. The observation and analysis unit as claimed in claim 14, wherein the X-ray detector is fitted in a revolving objective nosepiece.

16. The light microscope as claimed in claim 1, wherein the X-ray detector is fitted in the revolving objective nosepiece.

17. A light microscope, comprising:
- an electron beam source from which, in addition to or as an alternative to an illumination ray path coming from a light microscope objective, an electron beam is directed at a sample;
- an X-ray detector which receives X-ray radiation generated by interaction of the electron beam with the sample;
- an evaluation device that is operably coupled to the X-ray detector and spectrally analyzes the X-ray radiation;
- a shielding that prevents propagation of the X-ray radiation that is hazardous to person, wherein the shielding encloses the electron beam source, the X-ray detector, and the sample;
- a structure for feeding a non-air gas to a space between the sample and the electron beam source within the shielding; and
- a revolving objective nosepiece, wherein the electron source is integrated into the revolving objective nosepiece;
- wherein the sample is surrounded by a gas below or near atmospheric pressure, during analysis by application of the electron beam source and the X-ray detector.

\* \* \* \* \*